United States Patent [19]

Torossian et al.

[11] 4,098,803

[45] * Jul. 4, 1978

[54] ESTERS OF 21-THIOL-STEROIDS HYDROCORTISONE AND CORTISONE

[75] Inventors: Dieran Robert Torossian, Bourg-la-Reine; Gilbert Gustave Aubard; Jacky Marcel Legeai, both of Palaiseau, all of France

[73] Assignee: Jouveinal S.A., Val de Marne, France

[*] Notice: The portion of the term of this patent subsequent to Mar. 29, 1994, has been disclaimed.

[21] Appl. No.: 756,597

[22] Filed: Jan. 4, 1977

Related U.S. Application Data

[63] Continuation-in-part of Ser. No. 473,388, May 28, 1974, Pat. No. 4,014,909.

[30] Foreign Application Priority Data

May 30, 1973 [FR] France .................. 73 19734

[51] Int. Cl.² .................................. C07J 31/00
[52] U.S. Cl. .................. 260/397.45; 424/243
[58] Field of Search ......................... 260/397.45

[56] References Cited

U.S. PATENT DOCUMENTS

| | | | |
|---|---|---|---|
| 2,814,632 | 11/1957 | Nussbaum | 260/397.45 |
| 3,803,133 | 4/1974 | Vogt | 260/397.45 |
| 3,959,260 | 5/1976 | Phillipps et al. | 260/397.45 |

OTHER PUBLICATIONS

"Merck Index" (1976) 9th Ed. p. 328.

*Primary Examiner*—Elbert L. Roberts
*Attorney, Agent, or Firm*—Charles E. Baxley

[57] ABSTRACT

The present invention relates to new esters of the 21-thiol-steroids, having the general formula given at (I) below, and also to a method of preparation of these new esters.

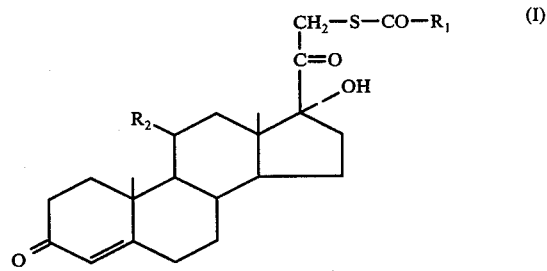

in which:
$R_1$ represents an alkyl radical comprising a number of carbon atoms between 4 and 9, or the para-fluorophenyl radical;
$R_2$ represents hydroxyl or the ketone function.

The esters of the invention have a considerable anti-inflammatory activity but also have small systemic effects and are applied especially to the local treatment of inflammatory illnesses.

29 Claims, No Drawings

ESTERS OF 21-THIOL-STEROIDS HYDROCORTISONE AND CORTISONE

CROSS REFERENCE

The present application is a continuation in part application of application Ser. No. 473,388, filed May 28, 1974, now U.S. Pat. No. 4,014,909.

BACKGROUND OF INVENTION

The present invention relates to new esters of the 21-thiol steroids having the general formula given at (I) below

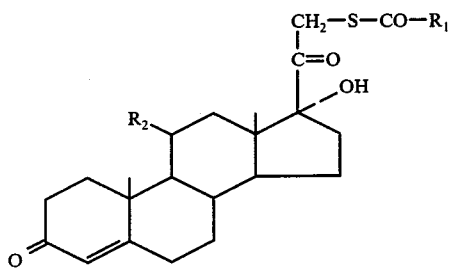

in which:
R$_1$ represents an alkyl radical comprising a number of carbon comprised between 4 and 9 atoms of carbon, or the parafluoro-phenyl radical;
R$_2$ represents hydroxyl or the ketone function.

Several publications describe the modification of the group 21-hydroxy-methyl of the corticoids, and more particularly the replacement of the oxygen of this function by sulphur.

Thus, the 21-thio-acetate of hydrocortisone is synthetized and declared free of any interesting biological activity (J. Org. Chem. 26,1223, 1961).

Other derivatives have been proposed as anti-inflammatory products having solely a systemic action on the system or a local action and a systemic action:

The 21-thio-acetate and 21-thio propionate of prednisolone (U.S. Pat. No. 2,814,632) have been described as possessing an adreno-corticoid activity accompanied by considerable diuretic activity.

The 21-thio-acetate of dexamethasone (French Pat. No. 1187 M) has been proposed as an anti-inflammatory product with a local action and a systemic action.

The therapeutic use of corticoids having a systemic action generally gives rise to harmful "secondary effects" (Presse Medicale No. 31,1419-1423, 1970).

These secondary effects comprise mainly: endocrine troubles, sodium retention accompanied by a leakage of potassium, weakening of the defense reactions of the organism, which result in a pro-infection effect, digestive ulcers and disturbances of the glucidic, proteic and lipidic metabolisms.

The number and the variety of these secondary effects necessitate a certain prudence and careful supervision during the use of these products.

The present invention has for its object to find a remedy for these disadvantages.

STATEMENT OF INVENTION

It has been found that, in a surprising manner, the structures forming the object of the present invention comprising a thio-alkanoic group of higher molecular weight, possess a considerable anti-inflammatory activity but they have only small systemic effects. The therapeutic doses thus remain very remote from those capable of causing the appearance of the secondary effects previously described.

Thus, certain substances according to the invention possess a thymolytic activity 100 times less than that of the glyco-corticoid of reference, whereas in the other hand their local anti-inflammatory activity is greater than that of the same reference.

Generally speaking, the substances forming the object of the present invention have shown a strongly reduced or nul activity on the glucidic and proteic metabolisms, little or no regression of the adrenal glands, no sodium retention.

In consequence, these substances are therapeutic agents having a very high safety in use, and this applies even in heavy doses, which find their application in the local treatment of inflammatory affections, such as the following:

Cutaneous illnesses and mucous illnesses that can be treated by corticoids;
Auto-rhino-laryngological and opthalmological illnesses of an inflammatory and/or allergic nature;
Low digestive inflammations such as colities, rectocolities, and and recto-sigmoiditis;
Collagen troubles, articular and rhumatismal illnesses;
Asthma, emphysema and respiratory fibrosis.

In addition, and contrary to the corresponding non-sulphurous steroids, these products have a long period of action free from "rebound effect" which is of great interest in the treatment of chronic inflammatory illnesses.

DESCRIPTION OF PREFERRED EMBODIMENTS

According to the invention, the new esters of the 21-thiol steroids are prepared by condensation between:

on the one hand iodized derivatives having the general formula (II):

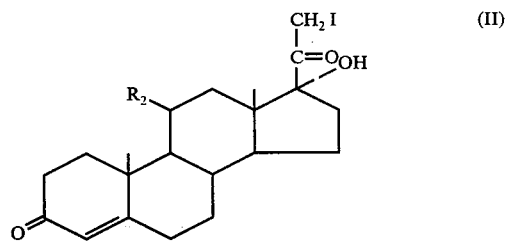

in which R$_2$ have the same signification as before;

on the other hand, S-thio-carboxylic acids utilised in their salified form, preferably in the form of the alkaline salts of these acids, especially the sodium salt. As S-thio-carboxylic acids, there are employed acids such as:

The thio-alkanoic acids comprising a number of carbon atoms comprised between 5 and 10, for example the S-thio-pivalic acid, the S-heptanethioic acid, the S-decanethioic acid and the S-pentanethioic acid, the S-methyl-2 butanethioic acid, the S-methyl-3 butanethioic acid, the S-hexanethioic acid, the S-methyl-4 pentanethioic acid, the S-dimethyl-3.3 butanethioic acid, the S-ethyl-2 butanethioic acid, the S-octanethioic acid, the S-ethyl-2 hexanethioic acid, the S-nonanethioic acid.

The parafluoro S-thiobenzoic acid is also used.

In order to salify the S-thio-carboxylic acid, the procedure is preferably as follows:

The solvent, preferably anhydrous acetone, and the S-thio-carboxylic acid are introduced into the reactor while stirring.

Then the sodium is introduced, preferably in the form of a methanol solution of sodium methylate, which is added drop by drop.

The operating conditions of the process of condensation of the iodized derivatives of Formula II and the alkaline S-thio-carboxylates are variable; however, the operation is generally carried out in the following manner:

There are introduced into a reactor comprising a reflux condenser, mechanical stirrer, the reaction solvent, especially anhydrous acetone, and then the iodized derivative of Formula II; to the suspension or solution thus formed there is added the acetone solution of the alkaline salt of S-thio-carboxylic acid previously prepared. The reaction medium is brought up to reflux and the solvent is then eliminated by distillation under vacuum.

It must be noted however that it is also possible to effect the condensation by introducing the iodized derivatives of Formula II in the powder form or in an acetone solution in the solution of sodium salt of S-thio-carboxylic acid and continuing the reaction as previously described.

The product obtained is purified depending on the case, either directly by crystallization from an alcohol having a low molecular weight or by column chromatography followed by a crystallization from the appropriate solvent or mixed solvents.

The molar ratio between the alkaline S-thio-carboxylate and the iodized derivative of Formula II employed is comprised between 1.4 mol of alkaline salt per mol of iodized derivative and 14 mols of alkaline salt per mol of iodized derivative.

The reaction temperatures are determined in dependence on the nature of the solvent and are in principle comprised between 56° C. and 102° C.

The time of the condensation reaction is favorably comprised between half an hour and 8 hours and preferably between 1 hour and 3 hours. For these reaction periods and according to the reactants utilized, the yields are substantially comprised between 12.5% and 90%. Generally speaking, the time of the reaction is determined in such a manner as to limit the formation of secondary derivatives.

In order to define the characteristics of the ester of the 21-thiol steroids thus prepared, analytic chemical methods are utilized, such as functional analysis and elementary centesimal analysis, and physico-chemical methods such as the ultra-violet and infra-red spectra.

The method which has just been described in general terms has been utilized for a whole variety of radicals $R_1$; it will be seen in particular in connection with the non-limitative examples which follow below. These examples have been chosen in such manner as to define the utilization of the method according to the invention for at least one type of radical belonging to the families claimed hereinafter.

EXAMPLE 1

DIHYDROXY -11β, 17α THIOL -21 DIOXO -3.20 PREGNENE-4 21 PIVALATE (JO. 1016).

In a reactor of 50 liters equipped with a dropping funnel, a mechanical stirrer and a calcium chloride tube to protect the apparatus from moisture, sodium S-thiopivalate is prepared from 100 grams of S-thiopivalic acid (0.844 mol), 214 cu.cm. of solution of sodium methylate, 3.95 M (0.844 mol.) in 25 liters of anhydrous acetone.

There are then added 285 grams (0.063 mol.) of dihydroxy-11β, 17αiodo-21 dioxo-3.20 pregenene-4 and the mixture is brought up to the acetone reflux for two hours. The solvent is eliminated by distillation under vacuum until there is obtained a syrupy residue which is poured into 10 liters of iced water. The insoluble part is filtered and dried under vacuum.

The crude product is purified by recrystallization from ethanol; weight: 250 grams ; yield : 89.5%

Analysis :

$C_{26}H_{38}O_5S$ : Calculated % : C,67.50; H,8.28; S,6.99. Found % : C,67.60; H,8.16; S,7.09.

Physical characteristics :

M.P = 195° - 200° C; $(\alpha)_D^{20}$ = + 145°, (dioxanne : c = 1%; λmax. (methanol) at 229 nm, $\log_{10} \epsilon$ = 4.259; Main absorptions of infra-red spectrum (KBr pellet) : 1722, 1688, 1660, 1623, 1368, 1237, 1116, 1038, 858 and 720 $cm^{-1}$.

EXAMPLE 2

DIHYDROXY - 11β, 17α THIOL--21 DIOXO - 3.20 PREGNENE-4 HEPTANOATE (J01027)

In a one liter three necked round bottomed flask equipped with a dropping funnel, a mechanical stirrer and a calcium chloride tube to protect the apparatus from moisture, there are introduced successively 400 cu.cm. of anhydrous acetone and 13.22 grams of S-heptanethioic acid (90 mmols).

22.8 cu.cm. of a methanol solution of sodium methylate 3.90 M (89 mmols) are introduced drop by drop in 12 minutes.

There is no modification of temperature, but the initial pale yellow colour becomes darker. After the introduction, stirring is continued for 5 minutes.

On the other hand, in a reactor of 10 liters fitted with a mechanical stirrer, a dropping funnel and a thermometer and reflux condenser protected from moisture by a calcium chloride tube, there are introduced 4 liters of anhydrous acetone followed by 30 grams (63.5 mmols) of dihydroxy-11β -17α iodo-21 dioxo-3.20 pregnene-4.

To this suspension, the acetone solution of sodium S-heptanethioate prepared above is introduced while stirring in 30 minutes. There is no change in temperature, the medium turns yellow and the product dissolves gradually.

The solution is brought up to the acetone reflux for 2 hours and then the solvent is eliminated by distillation under vacuum. The yellow oily residue is poured into 1.2 liters of water filtered and dried under vacuum at 40° C.

The crude product is isolated by the usual method and purified by column chromatography on 300 grams of mixture of magnesium oxide and silicon oxide (15-85) W/W (80–100 mesh). After elution with benzene which enables the by-products to be eliminated, elution by chloroform gives 22.4 grams of product which are crystallized from ethanol-hexane mixture, weight : 13.6 grams; yield : 43.6%.

Analysis : $C_{28}H_{42}O_5S$ : Calculated : C,68.53; H,8.63; S,6.53. Found % : C,68.66; H,8.47; S,6.44.

Physical characteristics : M.P 118° C; $(\alpha)_D^{20} = +135°$, (dioxanne : c = 1,2%); $\gamma$ max. (methanol) at 237.5 nm, $\log_{10}\epsilon = 4.287$; Main absorptions of intra-red spectrum (KBr pellet) : 1728, 1692, 1640, 1605, 1360, 1225, 1122, 1035, 868 and 712 cm$^{-1}$

EXAMPLE 3

DIHYDROXY - 11β, 17α THIOL-21 DIOXO-3.20 PREGNENE-4 21 DECANOATE (J01048)

Carrying out the operation under the same conditions as in Example 2, from 5.13 grams of S - decanethioic acid (27.24 mmols) 7.2 cu.cm. of sodium methylate solution 3.8 N (27.24 mmols) and 10.72 grams of dihydroxy-11β, 17α iodo-21 dioxo-3.20 pregnene-4 (22.7 mmols) there are obtained after treatment and crystallisation from ethanol 9.9 grams of white crystals; yield : 81.8%.

Analysis : $C_{31}H_{48}O_5S$ : Calculated % : C,69,89; H,9,08; S,6,02. Found % : C,69,81; H,9,04; S,6,01.

Physical characteristics : M.P. = 136° - 139° C; $(\alpha)_D^{20} = +133°$ (dioxanne, c = 1%); $\lambda$ max. (methanol) at 238 nm, $\log_{.10}\epsilon = 5,29$; Main absorptions of infr-red spectrum (KBr pellet) : 2920, 2850, 1780, 1625, 1270, 1235, 1130, 1110, 880 and 720 cm$^{-1}$ By proceeding in the manner of EXAMPLE 2, but with S-thioalkanoics acids indicated in Column 1 below the thio esters of Column 2 are obtained.

| COLUMN 1 | COLUMN 2 |
|---|---|
| S - pentanethioic acid | dihydroxy-11β, 17α thiol-21 dioxo-3.20 pregnene-4 21 pentanoate |
| S - methyl-2 butanethioic acid | dihydroxy-11β, 17α thiol-21 dioxo-3.20 pregnene-4 21 methyl-2 butanoate |
| S - methyl-3 butanethioic acid | dihydroxy-11β, 17α thiol-21 dioxo-3.20 pregnene-4 21 methyl-3 butanoate |
| S - hexanethioic acid | dihydroxy-11β, 17α thiol-21 dioxo-3.20 pregnene-4 21 hexanoate |
| S - methyl-4 pentanethioic acid | dihydroxy-11β, 17αthiol-21 dioxo-3.20 pregnene-4 21 methyl-4 pentanoate |
| S - dimethyl-3.3 butanethioic acid | dihydroxy-11β, 17α thiol-21 dioxo-3.20 pregnene-4 21 dimethyl-3.3 butanoate |
| S - ethyl-2 butanethioic acid | dihydroxy-11β, 17α thiol-21 dioxo-3.20 pregnene-4 21 ethyl-2 butanoate |
| S - octanethioic acid | dihydroxy-11β, 17α thiol-21 dioxo-3.20 pregnene-4 21 octanoate |
| S - ethyl-2 hexanethioic acid | dihydroxy-11β, 17α thiol-21 dioxo-3.20 pregnene-4 21 ethyl-2 hexanoate |
| S - nonanethioic acid | dihydroxy-11β,17α thiol-21 dioxo-3.20 pregnene-4 21 nonanoate |

EXAMPLE 4

DIHYDROXY - 11β, 17α THIOL - 21 DIOXO - 3.20 PREGNENE - 4 - 21 p. FLUORO-BENZOATE (J01026)

Carrying out the operation under the same conditions as in Example 2, from 42 grams of S-p. fluoro-thio-benzoic acid (0.269 mol.), 73.5 cu.cm. of sodium methylate solution 3.66 M (0.269 mol) and 72 grams of dihydroxy-11β, 17α iodo-21 dioxo-3.20 pregnene-4 (0.153 mol), there are obtained after treatment and crystallization from methanol 22 grams of pale pink crystals. Yield 32 28.8%.

Analysis : $C_{18}H_{33}FO_5S$ : Calculated % : C,67.17; H,6.64; F,3.80; S,6.41. Found % : C,67.31; H,6.34; F,3.73; S,6.43.

Physical characteristics : M.P = 225° - 230° C; $(\alpha)_D^{20} = +165°$, (dioxanne : c = 1,2%); $\lambda$ max. (methanol) at 236,5 nm, $\log_{10}\epsilon = 4.516$; Main absorptions of infra-red spectrum (KBr pellet) : 1717, 1670, 1635, 1600, 1508, 1235, 1210, 1115, 920, 848 and 720 cm$^{-1}$.

EXAMPLE 5

HYDROXY - 17α THIOL - 21 TRIOXO - 3,11,20 PREGNENE - 4 21 - PIVALATE (J01034)

The sodium S-thiopivalate is prepared in the usual manner from 2.21 grams (18,7 mmols) of S-thiopivalic acid, 4.8 cu. cm. of methanol solution of sodium methylate 3.9 M (18.7 mmols) of anhydrous acetone.

The solution is introduced into an acetone solution of hydroxy-17α iodo-21 trioxo-3,11,20 pregnene-4 (13.4 mmols): 6,3 grams.

After reaction and treatments, the product is purified by crystallization from 300 cu. cm. of methanol; weight = 32.5 grams; yield = 53%.

Analysis: $C_{26}H_{36}O_5S$: Calculated %: C,67.79; H, 7.88; S, 6.96. Found %: C, 67.93; H, 7.69; S, 6.78.

Physical characteristics: M.P = 213° - 215° C; $(\alpha)_D^{20} = +187.5°$, (dioxanne: c = 1%); $\lambda$ max. (methanol) at 235 nm, $\log_{.10}\epsilon = 4.307$; Main absorptions of infra-red spectrum (KBr pellet) 1700, 1675, 1650, 1365, 1230, 955 and 870 cm$^{-1}$

EXAMPLE 6

HYDROXY - 17α THIOL - 21 TRIOXO - 3,11,20 PREGNENE - 4 21 HEPTANOATE (JO 1035)

Under the same conditions as in the preceding example, from 8.25 grams (56,5 mmols) of S-heptanethioic acid and 14.5 cu. cm. of methanol solution of sodium methylate 3.9 M (56.5 mmols) on the one hand and 19 grams (4.4 mmols) of hydroxy-17α iodo-21 trioxo-3,11,20 pregnene-4 on the other hand, there is obtained a crude product which is purified by crystallisation from 100 ml of methanol: weight: 12.6 grams; yield: 63.9%.

Analysis: $C_{28}H_{40}O_5S$: Calculated %: C, 68.82; H, 8.25; S, 6.56. Found %: C, 68.98; H, 8.31; S, 6.47.

Physical characteristics: M.P = 125° - 126° C; $(\alpha)_D^{20} = +175°$, (dioxanne: c = 1%); $\lambda$ max. (methanol) at 234 nm, $\log_{.10}\epsilon = 4.286$; Main absorptions of infra-red spectrum (KBr pellet) 1700, 1655, 1275, 1050, 935 and 865 cm$^{-1}$

EXAMPLE 7

HYDROXY - 17α THIOL - 21 TRIOXO - 3,11,20 PREGNENE - 4 21 DECANOATE (JO 1049)

Under the same conditions as in Example 5, from 5.16 g of S - decanethioic acid (27.4 mmols), 7.2 cu. cm. of sodium methylate solution 3.8 N (27.4 mmols) and 10.75 g of hydroxy-17α iodo-21 trioxo-3,11,20 pregnene-4 (22.8 mmols), there are obtained after treatment and crystallisation from methanol 9.4 g of white product; yield = 77.7%.

Analysis: $C_{31}H_{46}O_5S$: Calculated %: C, 70,16; H, 8,74; S, 6,04. Found %: C, 69,89; H, 8.61; S, 6,04.

Physical characteristics M.P = 115° - 117° C; $(\alpha)_D^{20} = +175°$, (dioxanne, c = 1%); $\lambda$ max. (methanol) at 236 nm, $\log_{10}\epsilon = 5,291$; Main absorptions of infra-red spectrum (KBr pellet): 2920, 1680, 1650, 1360, 1270, 1220, 1050 and 935 cm$^{-1}$ By proceeding in the manner of Example 5, but with S-thioalkanoics acids indicated in Column 1 below the thio esters of Column 2 are obtained.

| COLUMN 1 | COLUMN 2 |
| --- | --- |
| S - pentanethioic acid | Hydroxy-17α thiol-21 trioxo-3,11,20 pregnene-4 21 pentanoate |
| S - methyl - 2 butanethioic acid | Hydroxy-17α thiol-21 trioxo-3,11,20 pregnene-4 21 methyl-2 butanoate |
| S - methyl - 3 butanethioic acid | Hydroxy-17α thiol-21 trioxo-3,11,20 pregnene-4 21 methyl-3 butanoate |
| S - hexanethioic acid | Hydroxy-17α thiol-21 trioxo-3,11,20 pregene-4 21 hexanoate |
| S - methyl -4- pentanethioic acid | Hydroxy-17α thiol-21 trioxo-3,11,20 pregnene-4 21 methyl-4 pentanoate |
| S - dimethyl - 3,3 butanethioic acid | Hydroxy-17α thiol-21 trioxo-3,11,20 pregnene-4 21 dimethyl-3,3 butanoate |
| S - ethyl - 2 butanethioic acid | Hydroxy-17α thiol-21 trioxo-3,11,20 pregnene-4 21 ethyl-2 butanoate |
| S - octanethioic acid | Hydroxy-17α thiol-21 trioxo-3,11,20 pregene-4 21 octanoate |
| S - ethyl - 2 hexanethioic acid | Hydroxy-17α thiol-21 trioxo-3,11,20 pregnene-4 21 ethyl-2 hexanoate |
| S - nonaethioic acid | Hydroxy-17α thiol-21 trioxo-3,11,20 pregnene-4 21 nonanoate |

EXAMPLE 8

HYDROXY - 17α THIOL - 21 TRIOXO - 3,11,20 PREGNENE - 4 21 p. FLUOROBENZOATE (JO 1046)

Carrying out the operation under the same conditions as in Example 5, from 4.28 grams of S-p. fluoro-thiobenzoic acid (27.4 mmols), 7.2 cu.cm. of sodium methylate solution 3.8 N (27.4 mmols) and 10.72 grams of hydroxy-17α iodo-21 trioxo-3,11,20 pregnene-4 (22.8 mmols), there are obtained after treatment and crystallisation from ethanol 5.5 grams of product. Yield = 48.4%.

Analysis: $C_{28}H_{31}FO_5S$: Calculated %: C, 67.45; H, 6.26; F, 3,81; S, 6,43. Found %: C, 67.35; H, 6.24; F, 3,75; S, 6,33.

Physical characteristics: M.P = 166° – 169° C; $(\alpha)_D^{20}$ = + 196°, (dioxanne, c = 1%); λ max. (methanol) at 239 nm, $\log_{10} \epsilon$ = 5,426; Main absorptions of infra-red spectrum (KBr pellet): 2930, 1700, 1595, 1500, 1230, 1205, 920 and 850 cm$^{-1}$

PHARMACOLOGICAL STUDY

There will now be described the tests which have enabled the determination of the pharmaco-dynamic properties of the esters of the 21-thiols steroids according to the invention.

ANTI-INFLAMMATORY ACTIVITY

The experimental local anti-inflammatory activity of the compounds presented was estimated in rats by their anti-proliferative (anti-granulomatous) action, and for one of these, by its anti-arthritic activity and its anti-exudative activity.

a. Anti-proliferative Activity

The anti-proliferative (anti-granulomatous) activity has been brought into evidence by means of a test, the principle of which is as follows.

The introduction of a foreign body into an organism produces a set of inflammatory reactions which results, in the chronic stage, in the formation of a defence granuloma around the foreign body. The proliferation of this granuloma is eliminated or attenuated by anti-inflammatory agents.

The technique employed is very similar to that described by Winter and Porter (J. Am. Pharm. Ass. 46/9. 515 1957) with rats.

Homogeneous groups of 10 male adult rats of the Wistar Strain were used, distributed at random and having weights comprised between 180 and 200 grams.

The implants or pellets were prepared from rolls of dental cotton; the weight of the pellets was between 35 and 40 mg.

Immediately before their introduction, the pellets were soaked with an antibiotic solution (0.1 ml. of a solution of penicillin G and streptomycin containing 200 000 UI of penicillin G and 0.1 gram of streptomycin sulphate per cc.)

Each animal received two pellets in the sub-cutaneous dorsal tissue on each side of the spinal column, at the costo-lumbar angle, under light anaesthesia with ether. The day of the operation and for three days after, the animals received by sub-cutaneous injection, 0.1 ml. of the antibiotic solution in the caudal region.

Six days after the introduction, the animals were killed by inhalation of chloroform and the granulomae were extracted and weighed, (wet and dry), and then the initial weights of the cotton pellets were substracted from the total weight.

Certain non-sulphured steroids causing a large increase in protein catabolism which can influence the formation of the granuloma independently of their anti-inflammatory action, the weights of the granulomae were expressed as a percentage of the body weight (technique proposed by G. Dipasquale and A. Meli: J. Pharm. Pharmacol. (1965), 17, 367-382) and the anti-proliferative effect of the various compounds as a percentage inhibition with respect to the reference granulomae. The $ED_{50}$ were calculated by transferring the results on semi-logarithmic paper.

a - 1. Local anti-inflammatory Activity

For this study, the products to be tested were dissolved in chloroform or in dimethylsuphoxide (DMSO) and the solutions obtained, deposited on the pellets at a volume of 0.2 ml per pellet. The solvent was then evaporated under high vacuum at ambient temperature, the complete elimination of the solvent being checked by weighing the pellets. "Reference" pellets, soaked with the solvent alone, were treated in the same manner.

a - 2. Systemic anti-inflammatory Activity

For this study, each animal received two untreated pellets. The product are given by oral route, daily during six days; the first administration began about 2 hours after the implantation.

The products were administered in suspension in a solution of arabic gum at 5% (w/v), at a volume of 1 ml/rat.

b. Anti-exudative Action

The anti-exudative activity was brought into evidence by means of a test, the principle of which is as follows.

This test consists of creating, under the dorsal skin of the rat an air pouch in which an irritant product is injected. An inflammatory reaction appears rapidly and is shown by the accumulation of liquid in the pouch of air.

The introduction of an anti-inflammatory product into the air pouch, reduced more or less completely, the accumulation of exudate.

This study was carried out with male rats of the Wistar strain, the initial weight of which was between 160 and 180 grams, following the technique described by M. Fukuhara and S. Tsurufuji (Biochem. Pharmac. 18, 475-484, 1969). Each lot comprised ten animals distributed at random.

Twenty-four hours before the beginning of the test, each animal received a sub-cutaneous injection of 6 ml. of air in the dorsal region; previously shaved.

The following day, 4 ml. of a 2% carrageenan solution in the physiological solution (NaCL at 0.9%), were injected in the pouch, the solution being kept lukewarm to prevent setting in a lump.

An injection of 0.1 ml. of a solution of penicillin and streptomycin containing 200 000 UI of penicillin and 0.1 gram of streptomycin per ml. was carried out immediately afterwards in the caudal region by sub-cutaneous methods.

Ninety-six hours after the administration of the carrageenan, the products under study were injected into the pouch in a volume of 0.2 ml, in suspension in carboxymethyl-cellulose at 0.5%.

Ninety-six hours after this last injection, the animals were killed and the exudate contained in the pouch was collected through a small incision made with a scalpel, and its volume was measured in a test tube.

The difference in volume of the exudate between the animals treated and the control lot was expressed as a percentage inhibition. The $ED_{50}$ were determined by transferring these results on to semi-logarithmic paper.

c. Anti-arthritic Activity

The anti-arthritic activity was brought out by means of a test, the principle of which is as follows:

This test was carried out following a method derived from that described by Foldi-Borcsok and Coll.(Arzneimittel Forschung 21, 2025-2030, 1971).

The injection of kaolin in the tibio-metatarsal joint of the rat causes an inflammation which develops in two successive phases:
  an acute phase characterized by an oedema of the joint;
  a chronic phase which follows, characterized by the proliferation of an inflammatory granuloma.

The intensity of the inflammatory reaction is estimated following the width of the articulation.

Male rats of Wistar stock were utilized, the initial weight of which was between 180 and 200 grams. Each group comprised ten animals taken at random, in which the width of the right-paw tibio-metatarsal joint was measured to the nearest 1/20th of a millimeter.

All the animals received 0.05 ml. of suspension of kaolin at 10% in a 0.9% physiological solution by intra-articular injection in the right-paw tibio-metatarsal joint.

Eighteen hours after this injection, the width of the joint was measured (initial inflammation) and there was then carried out an intra-articular injection of the products under study, in suspension in 0.5% carboxy-methyl-cellulose at a volume of 0.05 ml. The animals belonging to the control lot received 0.05 ml of the vehicle by the same method.

Twenty-four hours after this last injection, the width of the joint treated was again measured and then daily for 9 or 10 days, according to the evolution of the animals of the control group. The variation of width of the joints treated, representing the anti-arthritic activity of the products under study, were expressed as a percentage of the initial inflammation according to the formula:

$$\text{Anti-arthritic activity on the Nth day} = \frac{\Delta_1 - \Delta_n}{\Delta_1} \times 100$$

in which:
  $\Delta_1$ = increase in width of the joint with respect to its initial width, during the initial inflammation;
  $\Delta_n$ = increase in width of the joint with respect to its initial width, on the day considered.

The calculations were carried out by using the averages of the individual results of each lot.

SYSTEMIC EFFECTS

The systemic effects of the compounds according to the invention were evaluated through the intermediary of their thymolytic activity and for some of these, their possible influence on the glucidic metabolism, the hydro-mineral equilibrium, the weight increase, the endocrine glands and the genital tractus was examined and also a possible ulcerogenic effect.

d. Thymolytic effect

The thymolytic effects have been examined by means of a test, the principle of which is as follows:

The repeated administration of a gluco-corticoid having a systemic activity causes an involution of the defence system of the organism, of which two organs belong to the reticuloendothelial system, the spleen and the thymus, this latter being the most sensitive to this action, especially with young animals. The thymic involution is estimated by weighing. The thymolytic effects was studied by two routes:
  1. local route (local effects)
  2. oral route (systemic effects)

d - 1. Local Effects

For this study, the products are administered locally on pellets, following the procedure $a_1$.

Six days after inplantation, the thymus are taken off and quickly weighed.

d - 2. Systemic Effects

For this study, the various products were injected daily by the oral or the sub-cutaneous route for four days, to young male rats of Wistar-strain, the initial weight of which was between 45 and 55 drams, distributed at random by groups of ten.

The products under study were administered at a volume of 0.2 ml. per animal for both routes, in suspension in:
  Carboxy-methyl-cellulose at 0.5% for sub-cutaneous injection;
  Gum arabic at 5% for the oral route.

The animals of the control groups received the same volume of the corresponding vehicle.

Ninety-six hours after the first administration, the animals were killed, the thymus glands being taken and weighed immediately.

For each animal, the weight of the thymus has been brought to 100 grams of body weight. The thymolytic activity of the products under study was then expressed as a percentage of regression of the thymus with respect to the animals of the control group and the $ED_{50}$ of each product tested was estimated by transferring the percentage inhibition obtained for each does on semilogarithmic paper.

e. Action on the Glucidic Metabolism

The action on the glucidic metabolism was investigated by means of a test, the principle of which is as follows:

Gluco-corticoid reduce the peripheral needs of the organism in glucose, they also increase the synthesis by the liver of glycogen (neo-glycogenesis). Their action on the glucidic metabolism is thus indicated:

1. By an increase of glycemia;
2. By a glycogenic overload on the liver and especially by the persistence of the hepatic stock of glycogen in the food-deprived animal, and treated with a gluco-corticoid by comparison with the non-treated animal.

e - 1. Action on Glycemia

This study was done after the subchronic administration of JO 1016.

There were utilised groups of ten male rats or ten female rats of SPRAGUE DAWLEY I. O. P. S. Strain which have received the products under study by subcutaneous methods, daily for four weeks.

The products were administered in suspension in 0.5% carboxy-methyl-cellulose under a volume of 0.5 ml per 100 grams of body weight in three different doses; the control animals receiving the same volume of the vehicle alone.

e - 2. Action on the Glycogenic Overload on the Liver

For this study, Wistar male rats were used; the initial weight of which was between 150 and 160 grams, distributed at random in groups of ten.

The products studied were administered by the oral route in suspension in 5% gum arabic, under a volume of 0.5ml. per 100 grams, the animals of the control group receiving the same volume of vehicles under the same condition.

The treatments were carried out daily for four days, a fifth administration being given 7 hours before killing the animals, which took place 96 hours after the first administration.

Eighteen hours before being killed, all the animals were put on a water diet, this period of fasting having proved sufficient to eliminate the hepatic stock of glycogen in the animals of the control group.

Immediately after killing the animals, a sample of the hepatic tissue was taken from the central lobe and weighed. Immediately afterwards, it was subjected to digestion in 30% potassium hydroxyde in a boiling water-bath for 20 minutes. The glycogen contained in the digestate was then dosed, following the technique described by R. O. Stafford, L.E. Barnes and Coll. (Proc. Soc. Exp. Med. 39/3, 371-374, 1955).

The content of glycogen in the liver samples has been expressed in grams of glycogen per 100 grams of hepatic tissue.

f. Action on the Hydro-mineral Metabolism

The action on the hydro-mineral metabolism was examined by means of a test, the principle of which is as follows:

The gluco-corticoids are not all free from mineral-corticoid effects (for example Hydro-cortisone). These latter are indicated by:

A reduced renal elimination of sodium (sodium retention)

A loss of potassium (potassium leakage), these two effects reproducing the action of aldosteron.

f - 1. After a Short-term Study (96 hours)

This study has been carried out on male Wistar rats having weights between 180 and 190 grams.

The animals were distributed at random in groups of ten.

The products under study were administered by the oral route in suspension in 5% gum arabic. The animals of the control group received the same volume of vehicle under the same conditions.

The treatments were carried out daily for four days. The renal functional exploratory test was effected 90 hours after the first administration of the product tested.

Eighteen hours before the test, the animals were completely deprived of food and water, this being subsequently maintained up to the end of the test.

Immediately before the renal functional test, the animals received an overdose by the oral route of physiological solution equal to 5% by volume of their body weight.

The urine passed during five hours was collected for each animal in a polyethylene tube.

The concentration of sodium was determined in each sample by flame photometry; the total quantity excreted was then calculated as a function of the corresponding volume of urine. The values obtained for each group were then compared following the Fisher Student method with the quantity of sodium excreted by the animals of the control group.

f - 2. After a Long Term Study (Daily administration for 4 weeks following the same procedure described in $e_1$.).

At the end of the treatment, the urine sodium excretion in 5 hours, and the serum ionogram were determined.

g. Action on the Protein Metabolism

The action on the protein metabolism was examined by means of a test, the principle of which is as follows:

The administration of gluco-corticoids results in a disturbance of the protein metabolism, which is shown by an exaggerated protein catabolism resulting in shrinking of the tissues objectified by an inhibition of growth in weight in the young animal and a loss of body weight in the adult animal.

e - 1. After a Short Term Study

For this study, immature rats of Wistar strain were utilized, the initial weight of which was between 45 and 55 grams, which were distributed at random groups of ten.

g - 1.1. Local Activity

For this study, the products are administered locally on pellets, like the described procedure in $a_1$. The animals are weighed before the implantation and six days after.

g -1.2. Systemic Activity

The products were administered daily for four days. The animals were weighed daily during the four days of treatment and 24 hours after the last dose.

The products tested were administered either orally or by sub-cutaneous injection, in suspension in 5% gum arabic for the oral route or in carboxy-methyl-cellulose at 5% for the sub-cutaneous method, the animals of the control group receiving the same volume of vehicle by the same method as the corresponding animals treated.

The average variation of the body weight during the 96 hours treatment was calculated for each group of animals.

g - 2. After a Long Term Study

The average variation of the body weight between the initial weight and the final weight after 4 weeks of treatment by JO 1016 by subcutaneous route are calculated.

h. Action on the Adrenals

The administration of corticoids may result in an inhibition of the secretion of the ante-hypophysiary hormone which is shown by a lowering of the effectiveness of the target glands:adrenals. This effect was evaluated after a short or a long term study.

h - 1. Short Term Study
h - 1.1. Local Effect

The products are administered locally on pellets following the described procedure $a_1$. Six days after the implantation, the adrenals are taken off and quickly weighed.

h - 1.2. Systemic Effects

The products are administered daily during six days. The products given are in suspension in a solution of arabic gum at 5% (w/v) by oral route, under a volume of 1 ml/rat. The day after the last administration, the adrenals are taken off and quickly weighed.

h - 2. Long Term Study (Daily administration for 4 weeks following the same procedure described in $e_1$). At the end of the study, the adrenals are taken off and quickly weighed, then are fixed in Bouin Holland for an histological examination The results are expressed in mg/100 gram s of bodyweight; the mean weights are calculated for each group.

i. Action on the Genital Tractus

The repeated administration of corticoids may result in an indirect action on organs which are under the dependance of an hormone secretion.

For this reason, after a sub-chronic administration with one product of the invention (cf $e_1$), the gonads (testicles or ovaries), the seminal tubes or the uterus are taken off and weighed. The results are expressed in mg/100 grams of bodyweight.

j. Action on the Digestive Tractus, and Pro-infectious Effect

The repeated administration of certain corticoids produced ulceration generally localised at the stomach.

After a sub-chronic administration with one product, the stomach, the duodenum, and some portions of the small intestine, ileon and colon are preleved, examined and fixed in the Bouin Holland for histological examination. Liver, kidneys, thymus and spleen are also preleved and examined.

RESULTS OF THE PHARMACOLOGICAL STUDY

There will now be described the results of the pharmacological study.

a. Anti-proliferative Activity
    a - 1. Local Anti-inflammatory Activity

The $ED_{50}$ obtained for each of the products presented and the corresponding steroids are indicated in Tables I and II below.

TABLE I

| | DERIVATIVES OF HYDRO-CORTISONE | |
|---|---|---|
| TREATMENT | WET WEIGHT OF PELLET | DRY WEIGHT OF PELLET |
| Hydrocortisone (base) | $ED_{50} = 10$ mg/pellet | $ED_{50} = 4,1$ mg/pellet |
| Hydrocortisone (acetate) | $ED_{50} = 1,05$ mg/pellet | $ED_{50} = 0,80$ mg/pellet |
| JO 1016 | $ED_{50} = 0,35$ mg/pellet | $ED_{50} = 0,18$ mg/pellet |
| JO 1026 | $ED_{50} = 0,40$ mg/pellet | $ED_{50} = 0,23$ mg/pellet | in considering the dry weight of the granulomae, it is clear that the local anti-inflammatory activity of compounds JO 1016 and JO 1026 respectively is approximatively 4,5 times and 3,5 times greater than the activity of the reference compound, hydrocortisone acetate.

TABLE II

| | DERIVATIVES OF CORTISONE | |
|---|---|---|
| TREATMENT | WET WEIGHT OF PELLET | DRY WEIGHT OF PELLET |
| Cortisone acetate | $ED_{50} = 17$ mg/pellet | $ED_{50} = 0,70$ mg/pellet |
| JO 1034 | $ED_{50} = 7$ mg/pellet | $ED_{50} = 0,40$ mg/pellet |

When administered by oral route, compound JO 1034 exerts an antiinflammatory activity nearly twice that of the corresponding activity of the reference a - 2. Systemic Anti-inflammatory Activity The $ED_{50}$ obtained are indicated in Table III

TABLE III

| | DERIVATIVES OF CORTISONE (ORAL ROUTE) | |
|---|---|---|
| TREATMENT | WET WEIGHT OF PELLET | DRY WEIGHT OF PELLET |
| Cortisone acetate mg/Rat | $ED_{50} = 150$ mg | $ED_{50} = 19,8$ mg |
| JO 1034 mg/Rat | $ED_{50} > 750$ mg | $ED_{50} > 750$ mg |

The $ED_{50}$ are expressed as the total doses administered during six days, per rat.

It can be considered that, when administered by oral route, compound JO 1034 exerts an antiinflammatory activity about 40 times less than that of the corresponding activity of the reference compound, cortisone acetate.

b. Anti-exudative Activity

The results indicated on TABLE IV were obtained with the JO 1016.

TABLE IV

| | Anti-exudative activity |
|---|---|
| Hydrocortisone acetate | $ED_{50} = 1.5$ mg |
| JO 1016 | $ED_{50} = 1.5$ mg |

When administered by local route, compound JO 1016 exerts the same anti-exsudative activity as hydrocortisone acetate.

c. Anti-arthritic Activity

For example, the results obtained are referred to:
    A derivative of hydrocortisone: JO 1016
    and also to the corresponding reference steroid.

The figures indicated in TABLE V below, represent the anti-arthritic activity of the products, estimated from the diminution in width of the joint (as a percentage of the initial inflammation), 24 hours after their injection and 120 hours after the injection. JO 1016 and its corresponding reference steroid were administered in a ratio of doses equal to the ratio of their respective molecular weights.

TABLE V

| | DOSE | 24 HOURS | 120 HOURS |
|---|---|---|---|
| Hydrocortisone acetate | 2,91 mg | −65,0% | −76,2% |
| JO 1016 | 3,34 mg | − 58,9% | − 81,2% |

When administered by local route, compound JO 1016 exerts an antiarthritic activity similar to that of hydrocortisone acetate.

d. Thymolytic Activity
  d - 1. Local Activity

The thymolytic activity by local route is expressed in TABLE VI

TABLE VI

| TREATMENT | No. OF RATS | WEIGHT OF THYMUS MEAN (MG) ± e.s. | % AND PROBABILITIES |
|---|---|---|---|
| CONTROL | 10 | 308,7 ± 13,10 | — |
| CORTISONE ACETATE 0,1 mg/pellet | 10 | 303,1 ± 10,90 | −1,8 N.S. |
| CORTISONE ACETATE 0,5 mg/pellet | 10 | 313,1 ± 13,62 | + 1,4 N.S. |
| CORTISONE ACETATE 2,5 mg/pellet | 10 | 187,7 ± 12,21 | − 39,2 p < 0,001 |
| CORTISONE ACETATE 12,5 mg/pellet | 10 | 26,9 ± 2,72 | − 91,3 p < 0,001 |
| JO 1034 0,01 mg/pellet | 10 | 320,3 ± 13,16 | ± 3,8 N.S. |
| JO 1034 0,05 mg/pellet | 10 | 297,3 ± 6,87 | − 3,7 N.S. |
| JO 1034 0,25 mg/pellet | 10 | 296,1 ± 9,07 | − 4,1 N.S. |
| JO 1034 1,25 mg/pellet | 10 | 312,3 ± 7,88 | + 1,2 N.S. |

When administered in efficient doses for local antiinflammatory activity, compound JO 1034 is completely free of thymolytic effect, whereas this is not the case for the reference compound, cortisone acetate.

d - 2. Systemic Activity

The $ED_{50}$ obtained for each products presented and for the corresponding steroids are indicated in Tables VII and VIII which follow. (The calculated $ED_{50}$ are the total doses administered during four days per rat of about 50 grams at the beginning of the study.

TABLE VII

| DERIVATIVES OF HYDROCORTISONE | | |
|---|---|---|
| TREATMENT | ORAL ROUTE | SUB-CUTANEOUS ROUTE |
| Hydrocortisone (base) : | 4 mg | 1.8 mg |
| Hydrocortisone (acetate) : | 4 mg | 0.68 mg |
| JO 1016 | 400 mg | 120 mg |
| JO 1026 | >40 mg | >40 mg |

When administered by oral route, compounds JO 1026 and JO 1016 exert a thymolytic activity 10 to 100 times less than the activity of the reference compound, hydro cortisone acetate. By subcutaneous route, the same two compounds have a thymolytic activity 60 to 180 times less than the activity of the same reference compound.

TABLE VIII

| DERIVATIVES OF CURTISONE | |
|---|---|
| TREATMENT | ORAL ROUTE |
| CORTISONE ACETATE | $ED_{50} = $ 12 mg |
| JO 1034 | $ED_{50} > 750$ mg |

When administered by oral route, compound JO 1034 exerts a thymolytic activity at least 60 times less than the corresponding activity of the reference compound, cortisone acetate.

Ratio of the Local Anti-inflammatory Activity to the Thymolytic Activity

The ratio of the local anti-inflammatory activity to the thymolytic activity is all the greater as these products possess a low anti-inflammatory activity ($ED_{50}$ high in the numerator) and a large thymolytic activity ($ED_{50}$ low in the denominator).

The ratio is indicated in TABLES IX AND X which follow:

TABLE IX

| DERIVATIVES OF HYDROCORTISONE | | |
|---|---|---|
| | $ED_{50}$ Anti-proliferative activity | |
| | $ED_{50}$ Thymolytic activity | |
| | Thymolytic activity determined by the oral route | Thymolytic activity determined by the subcutaneous route |
| HYDROCORTISONE (BASE) | 2.5 | 5.5 |
| HYDROCORTISONE (ACETATE) | 0.25 | 1.2 |
| JO 1016 | <0.003 | 0.0008 |
| JO 1026 | <0.01 | <0.01 |

This chart shows, on one hand, how significant the local antiproliferative activity of the compounds according to the invention is and, on the other hand, that these compounds are free of systemic thymolytic effect.

TABLE X

| DERIVATIVES OF CORTISONE | |
|---|---|
| | $ED_{50}$ Anti-proliferative activity |
| | $ED_{50}$ Thymolytic activity/oral Route |
| CORTISONE ACETATE | 1,4 |
| JO 1034 | <0,009 |

This chart shows the local antiproliferative activity of JO 1034 and the absence of systemic thymolytic effect.

e. Action on the Glucidic Metabolism
  e - 1. Action on Glycemia

The following TABLES XI AND XII indicate the value of glycemia in the control animals and in the animals treated for 4 weeks following and described procedure.

TABLE XI

| Male animals | Mean (g/litre) ± standard error | Number of Animals | Percentage of variation and Probabilities |
|---|---|---|---|
| CONTROL | 1.1±0.05 | 10 | |
| JO 1016-100 mg/kg | 1.2±0.04 | 10 | +16% p<0.01 |
| JO 1016-250 mg/kg | 1.2±0.05 | 10 | +15% 0.02<p<0.05 |
| JO 1016-500 mg/kg | 1.1±0.03 | 10 | N.S. |

N.S. : insignificant

TABLE XII

| Female animals | Mean (g/litre) ±standard error | Number of animals | Percentage of variation and Probabilities |
|---|---|---|---|
| Control | 1.00 ± 0.04 | 10 | |
| JO 1016-100 mg/kg | 1.10 ± 0.04 | 10 | +10% N.S. |
| JO 1016-250 mg/kg | 1.21 ± 0.03 | 10 | +21% p 0.01 |
| JO 1016-500 mg/kg | 1.10 ± 0.04 | 10 | +10% N.S. |

The charts XI et XII show that, after a repeated administration, compound JO 1016 does not modify glycemia; the meaningful variation which is noted remain within the normal physiological range of the animal having undergone the test.

e - 2. Action on the Glycogenic Overload on the Liver

Table XIII which follows, indicates the content of glycogen in the liver of the control animals and the treated animals for 96 hours, after a water diet of 18 hours.

TABLE XIII

| | | Glycogen in g/100 g of hepatic tissue |
|---|---|---|
| CONTROL | | 0.15 |
| Hydrocortisone acetate | 2 mg/kg | 0.19 |
| Hydrocortisone acetate | 5 mg/kg | 0.45 |
| Hydrocortisone acetate | 10 mg/kg | 0.46 |
| Hydrocortisone acetate | 20 mg/kg | 1.26 |
| Hydrocortisone acetate | 50 mg/kg | 2.49 |
| JO 1016 | 25 mg/kg | 0.25 |
| JO 1016 | 50 mg/kg | 0.39 |
| JO 1016 | 100 mg/kg | 0.42 |

Compound JO 1016 does not cause the formation of glycogen when administered in a dose of up to 100 mg/kg/. On the contrary, when administered in a dose 10 times less, hydrocortisone acetate causes a significant neoglycogenesis.

F. Action on the Hydro-mineral Metabolism f - 1. After a Short Term Study

The results obtained with hydrocortisone acetate and JO 1016 following the procedure described in $f_1$ are indicated in TABLE XIV.

TABLE XIV

| | mEq of sodium excreted Mean ± standard error | Number of Animals | Percentage of variation and Probabilities |
|---|---|---|---|
| CONTROL | 0.816 ± 0.0493 | 4 | |
| Hydrocortisone acetate - 16 mg/kg | 0.371 ± 0.0827 | 5 | −55% $0.001<p<0.01$ |
| JO 1016  16 mg/kg | 0.820 ± 0.1040 | 5 | 0.4% N.S. |
| JO 1016  32 mg/kg | 0.754 ± 0.0465 | 4 | −8% N.S. |
| JO 1016  80 mg/kg | 0.684 ± 0.1591 | 4 | −16% N.S. |
| JO 1016  160 mg/kg | 0.664 ± 0.0484 | 5 | −19% N.S. |

When administered in a dose 10 times greater than $ED_{50}$ of hydrocortisone acetate, compound JO 1016 does not induce sodium retention.

f - 2. After a Long Term Study

The result obtained in the case of a treatment lasting 4 weeks following the procedure described, are indicated in the following TABLE XV.

TABLE XV

| | mEq of sodium excreted Mean ± standard error | Number of Animals | Percentage of variation and Probabilities |
|---|---|---|---|
| CONTROL | | | |
| MALE RAT CONTROL | 1.77 ± 0.089 | 10 | — |
| FEMALE RAT | 1.77 ± 0.065 | 10 | — |
| JO 1016 male rat 500 mg/kg | 1.41 ± 0.116 | 10 | −20% $0.02<p<0.05$ |
| JO 1016 female rat 500 mg/kg | 0.91 ± 0.98 | 10 | −22% $0.02<p<0.05$ |

After having administered a dose of 500 mg/kg/day, for four weeks, a slight sodium retention is noted.

g. Action on the Protein Metabolism g - 1. After a Short Term Study g - 1.1.. Local Action The local action on the protein metabolism are expressed in TABLE XVI.

| TREATMENT | No. OF RATS | INCREASE OF BODY-WEIGHT Mean(g)±e.s. | % AND PROBA-BILITIES |
|---|---|---|---|
| CONTROL | 10 | 40,4 ± 2,09 | — |
| CORTISONE ACETATE 0,1 mg/pellet | 10 | 39,5 ± 1,77 | − 2,2 N.S. |
| CORTISONE ACETATE 0,5 mg/pellet | 10 | 37,0 ± 2,35 | − 8,4 N.S. |
| CORTISONE ACETATE 2,5 mg/pellet | 10 | 33,4 ± 2,05 | − 17,3 $p < 0,01$ |
| CORTISONE ACETATE 12,5 mg/pellet | 10 | 5,1 ± 2,02 | − 87,4 $p < 0,001$ |
| JO 1034 0,01 mg/pellet | 10 | 36,6 ± 2,12 | − 9,4 N.S. |
| JO 1034 0,05 mg/pellet | 10 | 40,6 ± 1,78 | + 0,5 N.S. |
| JO 1034 0,25 mg/pellet | 10 | 38,9 ± 1,70 | − 3,7 N.S. |
| JO 1034 1,25 mg/pellet | 10 | 35,8 ± 1,60 | − 11,4 N.S. |

The doses of compounds JO 1034 which exert a local antiinflammatory activity do not cause any proteolytic effect, this distinguishing this compound from the reference compound, cortisone acetate.

g - 1.2.. Systemic Action

The increases in weight of immature rats (45 to 55 grams) treated for 96 hours following the procedure g) by JO 1016, by the oral or the sub-cutaneous routes, or by JO 1034 and cortisone acetate by the oral rote, (average weight at the end of the study, less the average weight at the beginning) are indicated in the following TABLES XVII and XVIII.

TABLE XVII

| | ORAL ROUTE | SUB-CUTANEOUS ROUTE |
|---|---|---|
| CONTROL | 13 g | 14 g |
| JO 1016 1 mg/rat/day | — | 17 g |
| JO 1016 3 mg/rat/day | 14 g | — |
| JO 1016 10 mg/rat/day | 11 g | 16 g |
| JO 1016 30 mg/rat/day | 13 g | 16 g |
| JO 1016 100 mg/rat/day | 8 g | — |

When administered by oral route, compound JO 1016 starts to show a proteolytic activity only from 2g/kg/day.

TABLE XVIII

| TREATMENT (ORAL) ROUTE | No. OF RATS | INCREASE OF BODY WEIGHT Mean(g)±e.s | % AND PROBA-BILITIES |
|---|---|---|---|
| CONTROL | 10 | 21,4 ± 1,00 | — |

TABLE XVIII-continued

| TREATMENT (ORAL) ROUTE | No. OF RATS | INCREASE OF BODY WEIGHT Mean(g)±e.s | % AND PROBA- BILITIES |
|---|---|---|---|
| CORTISONE ACETATE 0,1 mg/Rat/jour | 10 | 20,6 ± 0,91 | −3,7 N.S. |
| CORTISONE ACETATE 0,5 mg/Rat/jour | 10 | 21,4 ± 1,06 | 0,0 N.S. |
| CORTISONE ACETATE 2,5 mg/Rat/jour | 10 | 17,4 ± 0,75 | −18,7 $p<0,01$ |
| CORTISONE ACETATE 12,5 mg/Rat/jour | 10 | 14,0 ± 1,11 | −34,6 $p<0,001$ |
| JO 1034 1 mg/Rat/jour | 10 | 24,0 ± 1,12 | +12,2 N.S. |
| JO 1034 5 mg/Rat/jour | 10 | 23,8 ± 1,20 | +11,2 N.S. |
| JO 1034 25 mg/Rat/jour | 10 | 24,5 ± 0,95 | +14,5 $p<0.01$ |
| JO 1034 125 mg/Rat/jour | 10 | 24,7 ± 1,73 | +15,4 N.S. |

This chart confirms that compound JO 1034 is free of activity, when administered by systemic route, contrary to the reference compond, cortisone acetate.

g - 2. After a Long Term Study

The weights of the animals at the end of the 4 weeks of treatment by JO 1016 by the sub-cutaneous route are indicated in the following TABLES XIX and XX.

TABLE XIX

| MALE RATS | MEAN (G) ± Standard error | NUMBER OF ANIMALS | PERCENT- AGES OF VARIATION AND PROBA- BILITIES |
|---|---|---|---|
| CONTROL | 296 ± 7.6 | 10 | |
| JO 1016 100 mg/kg | 299 ± 5.2 | 10 | N.S. |
| JO 1016 250 mg/kg | 289 ± 7.7 | 10 | N.S. |
| JO 1016 500 mg/kg | 274 ± 2.5 | 10 | − 7% $0.02<p<0.05$ |

TABLE XX

| FEMALE RATS | MEAN (G) ± standard error | NUMBER OF ANIMALS | PERCENT- AGES OF VARIATION AND PROBA- BILITIES |
|---|---|---|---|
| CONTROL | 218 ± 3.22 | 10 | |
| JO 1016 100 mg/kg | 219 ± 3.06 | 10 | N.S. |
| JO 1016 250 mg/kg | 216 ± 3.18 | 10 | N.S. |
| JO 1016 500 mg/kg | 198 ± 4.85 | 10 | −9% $0.001<p<0.01$ |

When administered for 4 weeks, compound JO 1016 does not modify the weight increase or the animals; the modification which is noted remains within the normal physiological range of the animals having undergone the test.

After 14 days of treatment by hydrocortisone acetate at corresponding ratio, by the sub-cutaneous route, weights of the animals are indicated in the following TABLE XXI.

TABLE XXI

| MALE RATS | MEAN (G) ± standard error | NUMBER OF ANIMALS | PERCENT- AGES OF VARIATION AND PROBA- BILITIES |
|---|---|---|---|
| CONTROL | 264 ± 4.33 | 10 | |
| Hydrocortisone acetate 218 mg/kg | 110 ± 2.10 | 8 | − 58.4 % $0.001<p<0.01$ |
| Hydrocortisone acetate 436 mg/kg | 105 ± 4.12 | 2 | − 60.2 % $0.001<p<0.01$ |

When administered for 14 days, the reference steroid (hydrocortisone acetate) causes the body weight to drop very significantly.

h. Action on the Adrenals h - 1. After a Short Term Study h - 1.1.. Local Effect The results are reported in the TABLE XXII.

TABLE XXII

| TREATMENT | NUMBER OR RATS | ADRENAL WEIGHT (mg) Mean ± standard error | PERCENT- AGES OF VARIATION AND PROBA- BILITIES |
|---|---|---|---|
| CONTROL | 10 | 25,8 ± 1,31 | — |
| CORTISONE ACETATE 0,1 mg/pellet | 10 | 24,6 ± 0,87 | − 4,7 N.S. |
| CORTISONE ACETATE 0,5 mg/pellet | 10 | 26,2 ± 0,99 | + 1,6 N.S. |
| CORTISONE ACETATE 2,5 mg/pellet | 10 | 24,3 ± 0,52 | − 5,8 N.S. |
| CORTISONE ACETATE 12,5 mg/pellet | 10 | 19,3 ± 1,03 | − 25,2 $p<0,001$ |
| JO 1034 0,01 mg/pellet | 10 | 26,5 ± 0,88 | + 2,7 N.S. |
| JO 1034 0,05 mg/pellet | 10 | 25,2 ± 1,09 | − 2,3 N.S. |
| JO 1034 0,25 mg/pellet | 10 | 26,7 ± 0,97 | + 3,5 N.S. |
| JO 1034 1,25 mg/pellet | 10 | 25,4 ± 0,39 | − 1,6 N.S. |

The doses of compounds JO 1034 which exert a local antiinflammatory activity do not cause any adrenolytic effect, this distinguishing this compound from the reference compound, cortisone acetate.

h - 1.2. Systemic Effect

The results are reported in the TABLE XXIII

TABLE XXIII

| TREATMENT | NUMBER OR RATS | ADRENAL WEIGHT (mg) Mean ± standard error | PERCENT- AGES OF VARIATION AND PROBA- BILITIES |
|---|---|---|---|
| CONTROL | 10 | 28,1 ± 1,02 | — |
| CORTISONE ACETATE 0,1 mg/Rat/jour | 10 | 28,5 ± 1,44 | + 1,4 N.S. |
| CORTISONE ACETATE 0,5 mg/Rat/jour | 10 | 27,4 ± 1,07 | − 2,5 N.S. |
| CORTISONE ACETATE 2,5 mg/Rat/jour | 10 | 23,0 ± 1,34 | − 18,2 $p<0,01$ |
| CORTISONE ACETATE 12,5 mg/Rat/jour | 10 | 22,2 ± 1,43 | − 21,0 $p<0,01$ |
| JO 1034 1 mg/Rat/jour | 10 | 29,0 ± 1,98 | + 3,2 N.S. |
| JO 1034 5 mg/Rat/jour | 10 | 27,8 ± 0,66 | − 1,1 N.S. |
| JO 1034 25 mg/Rat/jour | 10 | 28,8 ± 1,52 | + 2,5 N.S. |
| JO 1034 125 mg/Rat/jour | 10 | 27,1 ± 0,96 | − 3,6 N.S. |

This chart confirms that compound JO 1034 is free of systemic activity.

h - 2. After a Long Term study

The results are reported in TABLE XXIV. Weights are expressed per 100 grams of bodyweight. At the histological examination, neither atrophy nor hypertrophy was seen.

TABLE XXIV

|  | CONTROL | JO 1016 100 mg/kg | JO 1016 250 mg/kg | JO 1016 500 mg/kg |
|---|---|---|---|---|
| ADRENAL GLANDES (male rats) mg | 15.2 mg | 14.9 mg N.S. | 12.3 mg N.S. | 13.5 mg N.S. |
| ADRENAL GLANDES (female rats) | 25.1 mg | 26.7 mg N.S. | 24.5 mg N.S. | 27.0 mg N.S. |

After having administered compound JO 1016, for 4 weeks, in a dose up to 500 mg/kg/day, no adrenolytic is noted.

i. Action on the Genital Tractus

The results are expressed on the TABLE XXV. Neither modification of the functional aspect of the male and female genital organs are appeared.

TABLE XXV

|  | CONTROL | JO 1016 100 mg/kg | JO 1016 250 mg/kg | JO 1016 500 mg/kg |
|---|---|---|---|---|
| Testicles | 1.131 g | 1.143 g N.S. | 1.144 g N.S. | 1.207 g N.S. |
| Ovaries | 38.5 g | 38.4 mg N.S. | 38.3 mg N.S. | 39.3 mg N.S. |
| Seminal vesicles | 284.3 g | 328.0 mg N.S. | 296.0 mg N.S. | 274.6 mg N.S. |
| Uterins tubes | 150.4 g N.S. | 211.8 mg N.S. | 184.7 mg N.S. | 165.4 mg N.S. |

At the end of the same long term study, no activity on the genital tractus is noted.

j. Action on the Digestive Tractus and Pro-infectious Effects

The results of the macroscopic observations in indicated in TABLE XXVI

TABLE XXVI

| Organs examined | Macroscopic observation | 14 days of treatment with hydrocortisone acetate DOSES 218 mg/kg Case n° | 14 days of treatment with hydrocortisone acetate DOSES 436 mg/kg Case n° | 4 weeks of treatment with JO 1016 DOSES 250 mg/kg Case n° | 4 weeks of treatment with JO 1016 DOSES 500 mg/kg Case n° |
|---|---|---|---|---|---|
| LIVER | Presence of abscess | 7/8 | 1/2 | 0/10 | 0/10 |
| KIDNEYS | " | 2/8 | 1/2 | 0/10 | 0/10 |
| SPLEEN | Atrophied | 8/8 | 2/2 | 0/10 | 0/10 |
| THYMUS | Atrophied | 8/8 | 2/2 | 0/10 | 0/10 |
| STOMACH | Ulcerated | 6/8 | 2/2 | 0/10 | 0/10 |
|  | Ulcerated and infected | 4/8 | 2/2 | 0/10 | 0/10 |

This chart shows the difference between the indesirable general effects caused by hydrocortisone acetate when administered for 14 days, and the absence of corresponding effects after the administration of compound JO 1016 for 4 weeks.

POSOLOGY

The products described in the present invention are preferably utilized by local methods on the skin, the mucous membranes of the O.R.L. organ, the mucous membranes of the respiratory organs and the high and low digestive mucous.

The products are also used locally in the form of intra-articular injectable suspensions.

Generally speaking, the products are presented in the form of injectable, oral, nasal and auricular suspensions, of mouth-washes, gels and pomades, of suppositories, tablets and aerosols.

For the forms in which the product is in suspension, or may be considered as such, the active principle is utilized in the "micronized" form, the mean dimension of the particles being 2 microns.

The useful posology of the structures described by the present invention, as a function of their method of administration, extends between 0.25 and 50 mg. per unit taken and 1 to 200 mg. per day in adult animals.

The pharmaceutical forms may contain the products according to the invention, alone or associated with other therapeutic agents.

What we claim is:

1. New steroids compounds of the general formula:

[Chemical structure showing steroid with $CH_2-S-CO-R_1$, $C=O$, $OH$ at position 17, $R_2$ substituent, and ketone at position 3]

wherein:
$R_1$ is an alkyl radical having from 4 to 9 carbon atoms or is the p. fluorophenyl radical and $R_2$ is an hydroxyl radical or a ketone fonction.

2. The dihydroxy $11\beta$, $17\alpha$ thio-21 dioxo-3,20 pregnene-4 21-pivalate steroid compound of claim 1.

3. The dihydroxy $11\beta$, $17\alpha$ thio-21 dioxo-3,20 pregnene-4 21-heptanoate steroid compound of claim 1.

4. The dihydroxy $11\beta$, $17\alpha$ thio-21 dioxo-3,20 pregnene-4 21-decanoate steroid compound of claim 1.

5. The dihydroxy $11\beta$, $17\alpha$ thio-21 dioxo-3,20 pregnene-4 21-p. fluorobenzoate steroid compound of claim 1.

6. The dihydroxy $11\beta$, $17\alpha$ thio-21 dioxo-3,20 pregnene-4 21-pentanoate steroid compound of claim 1.

7. The dihydroxy $11\beta$, $17\alpha$ thio-21 dioxo-3,20 pregnene-4 21-methyl-2 butanoate steroid compound of claim 1.

8. The dihydroxy $11\beta$, $17\alpha$ thio-21 dioxo-3,20 pregnene-4 21-methyl-3 butanoate steroid compound of claim 1.

9. The dihydroxy $11\beta$, $17\alpha$ thio-21 dioxo-3,20 pregnene-4 21-hexanoate steroid compound of claim 1.

10. the dihydroxy 11β, 17α thio-21 dioxo-3,20 pregnene-4 21-methyl-4 pentanoate steroid compound of claim 1.

11. The dihydroxy 11β, 17α thio-21 dioxo-3,20 pregnene-4 21-dimethyl-3,3 butanoate steroid compound of claim 1.

12. The dihydroxy 11β, 17α thio-21 dioxo-3,20 pregnene-4 21-ethyl-2 butanoate steroid compound of claim 1.

13. The dihydroxy 11β, 17α thio-21 dioxo-3,20 pregnene-4 21-octanoate steroid compound of claim 1.

14. The dihydroxy 11β, 17α thio-21 dioxo-3,20 pregnene-4 21-ethyl-2 hexanoate steroid compound of claim 1.

15. The dihydroxy 11β, 17α thio-21 dioxo-3,20 pregnene-4 21-nonanoate steroid compound of claim 1.

16. The hydroxy-17α thiol-21 trioxo 3,11,20 pregnene-4 21-pivalate steroid compound of claim 1.

17. The hydroxy-17α thiol-21 trioxo 3,11,20 pregnene-4 21-heptanoate steroid compound of claim 1.

18. The hydroxy-17α thiol-21 trioxo 3,11,20 pregnene-4 21-decanoate steroid compound of claim 1.

19. The hydroxy-17α thiol-21 trioxo 3,11,20 pregnene-4 21- p. fluorobenzoate steroid compound of claim 1.

20. The hydroxy-17α thiol-21 trioxo 3,11,20 pregnene-4 21-pentanoate steroid compound of claim 1.

21. The hydroxy-17α thiol-21 trioxo 3,11,20 pregnene-4 21-methyl-2 butanoate steroid compound of claim 1.

22. the hydroxy-17α thiol-21 trioxo 3,11,20 pregnene-4 21-methyl-3 butanoate steroid compound of claim 1.

23. The hydroxy-17α thiol-21 trioxo 3,11,20 pregnene-4 21-hexanoate steroid compound of claim 1.

24. The hydroxy-17α thiol-21 trioxo 3,11,20 pregnene-4 21-methyl-4 pentanoate steroid compound of claim 1.

25. The hydroxy-17α thiol-21 trioxo 3,11,20 pregnene-4 21-dimethyl-3,3 butanoate steroid compound of claim 1.

26. The hydroxy-17α thiol-21 trioxo 3,11,20 pregnene-4 21-ethyl-2 butanoate steroid compound of claim 1.

27. The hydroxy-17α thiol-21 trioxo 3,11,20 pregnene-4 21-octanoate steroid compound of claim 1.

28. The hydroxy-17α thiol-21 trioxo 3,11,20 pregnene-4 21-ethyl-2 hexanoate steroid compound of claim 1.

29. The hydroxy-17α thiol-21 trioxo 3,11,20 pregnene-4 21-nonanoate steroid compound of claim 1.

* * * * *

UNITED STATES PATENT AND TRADEMARK OFFICE
CERTIFICATE OF CORRECTION

PATENT NO. : 4,098,803
DATED : July 4, 1978
INVENTOR(S) : Dieran Robert Torossian, Gilbert Gustave Aubard and Jacky Marcel Legeai It is certified that error appears in the above-identified patent and that said Letters Patent are hereby corrected as shown below:

Column 5, line 7 delete [intra] and insert infra therefor.

Column 6, line 1 delete [32].

line 3, delete [$C_{18}H_{33}FO_5S$] and insert $C_{28}H_{33}FO_5S$ therefor.

Column 11, line 7 delete [does] and insert dose therefor.

Column 16, line 56 delete [and] and insert the therefor.

Column 18, line 44 delete [increases] and insert increase therefor.

line 47, delete [rote] and insert route therefor.

Signed and Sealed this

Twenty-third Day of January 1979

[SEAL]

Attest:

RUTH C. MASON
Attesting Officer

DONALD W. BANNER
Commissioner of Patents and Trademarks